United States Patent [19]
Birnbaum et al.

[11] Patent Number: 4,580,575
[45] Date of Patent: Apr. 8, 1986

[54] APNEA MONITORING SYSTEM

[75] Inventors: Michael R. Birnbaum, St. Louis Park; Peter Stasz, Minneapolis, both of Minn.

[73] Assignee: Aequitron Medical, Inc., Minneapolis, Minn.

[21] Appl. No.: 660,458

[22] Filed: Oct. 12, 1984

Related U.S. Application Data

[63] Continuation of Ser. No. 388,016, Jun. 14, 1982, abandoned.

[51] Int. Cl.$^4$ ............................ A61B 5/04; A61B 5/05; A61B 5/08
[52] U.S. Cl. .................................... 128/671; 128/716; 128/723; 128/696; 128/706
[58] Field of Search ............... 128/671, 716, 721, 722, 128/723, 708, 702, 696, 706

[56] References Cited

U.S. PATENT DOCUMENTS

| | | | |
|---|---|---|---|
| 3,572,317 | 3/1971 | Wade | 128/671 |
| 3,976,052 | 8/1976 | Junginger et al. | 128/723 X |
| 4,192,318 | 3/1980 | Dam et al. | 128/708 |
| 4,250,889 | 2/1981 | Levin | 128/708 |
| 4,387,722 | 6/1983 | Kearns | 128/716 |
| 4,422,458 | 12/1983 | Kravath | 128/671 |
| 4,446,868 | 5/1984 | Aranson | 128/708 |

Primary Examiner—Kyle L. Howell
Assistant Examiner—John C. Hanley
Attorney, Agent, or Firm—Paul L. Sjoquist

[57] ABSTRACT

Apparatus for monitoring respiration and heartbeat and for processing electrical signals representative thereof, including circuits for developing a phase-shifted and amplitude-offset respiration signal for comparison with an original respiration signal for compensating for signal drift, and circuits for logically combining signals representative of the presence of respiration and heartbeat for eliminating certain false indications which may occur when only heartbeat exists.

13 Claims, 7 Drawing Figures

APNEA MONITORING SYSTEM

This is a continuation of U.S. patent application Ser. No. 388,016, filed June 14, 1982 now abandoned.

BACKGROUND OF THE INVENTION

This invention relates to an apparatus for monitoring patient respiration and heartbeat, and for processing representative signals received from the patient for the purpose of evaluating the condition of the patient's health; specifically, the invention provides an evaluation of the patient's respiration to detect the condition known as apnea, and to reliably detect this condition while rejecting false indications of the condition.

The medical term "apnea" means cessation of respiration or breathing. The apnea condition has become associated in recent years with the "sudden infant death syndrome", wherein a disturbing pattern of early deaths of apparently healthy infants has been noted. Studies and research programs have been conducted by agencies of the Federal Government and others in an attempt to identify the cause of sudden infant death syndrome, and such studies have revealed that infants who are subject to this syndrome are apparently not the healthy infants that they were once believed to be. These infants appear to have subtle anatomic and physiological defects of a neurologic, cardiorespirtory and/or metabolic nature. Evidence has developed that the syndrome is not caused by a single mechanism working at one moment in time, but rather by a number of developmental, environmental, and pathological factors which become combined in complex interactions and circumstances to set up a sequence of events that produces the sudden and unexpected infant death. Much of this research has revolved around the hypothesis that apnea during sleep is related to the syndrome. It has also been postulated that apneic episodes during sleep which do not necessarily lead to sudden infant death may lead to aberrations in central nervous system development. There is evidence that infants who have numerous apneic episodes during sleep will receive an inadequate oxygen supply to the brain, which may lead to retardation of brain development, and which in turn may lead to further loss of respirtory control and further apneic problems.

Apnea may be caused by a number of other factors not necessarily related to the condition of infants, some of which are spinal cord injury, muscular dystrophy, lung diseases, drug intoxication, and certain other risk factors which have become apparent in identifying those who might be candidates for apnea. In adults, a history of heavy snoring denotes an individual at risk to apnea, especially in combination with other factors such as obesity, underlying heart disease and/or high blood pressure.

Whereas apneic conditions may be monitored in hospital and laboratory environments by means of suitably connected electrodes to a patient's body, and monitoring of a cathode ray tube (CRT) display which exhibits a waveform related to patient respiration, such monitoring is impractical or impossible in less controlled environments. There is a need for techniques and devices which will enable appropriate monitoring of adults or infants and which will detect apnea in time to set off an alarm in order that the condition may be corrected. For sleeping patients, it is frequently only necessary to wake the patient by means of an audible alarm in order that the patient may become conscious and resume normal breathing. It is therefore important that techniques and devices be developed for utilization in conjunction with sleeping individuals, in order that apneic episodes may be detected and corrected before physiological damage or harm occurs. In all events, the detection of apnea requires a monitoring of respiration and/or heart rates. Such monitoring is accomplished by means of the attachment or coupling of suitable electrodes or other transducer devices to the patient, so that signals developed by such devices may be transmitted to circuitry for detection and analysis. Monitoring transducers are well-known in the art, usually taking the form of electrical contacts attached in good electrical conductivity with several points on the patient's body, together with a suitable electrical circuit for monitoring minute impedance changes and electrical voltages developed by respiration and cardiac activity. Other forms of transducers have been developed utilizing pressure sensing techniques, and which monitor pressure changes occurring in various parts of the body as body movement occurs during respiration. All of these transducers monitor a physical parameter which is correlated with respiration and/or heartbeat, and convert the parameter monitored into an equivalent electrical signal, and feed the signal into appropriate circuitry whose ultimate function is to note the occurrence of a respiration cycle and to perform such other functions as are deemed necessary.

SUMMARY OF THE INVENTION

The present invention includes an electronic apparatus for receiving and processing electrical signals representative of heart rate and respiration, and for generating an alarm condition when the processing indicates that the condition of apnea is present in the patient. The invention includes circuitry for developing an in-phase and phase-shifted EKG and respiration signal, and for voltage-offsetting one of these signals, and for comparing the signals at predetermined points to compensate for inherent drifting of the raw respiration signal received from the patient. Further, the invention includes circuitry for receiving electrical signals representative of heartbeat and circuitry for triggering at a predetermined heartbeat signal amplitude and blanking for a predetermined time thereafter, thereby eliminating spurious signals generated by the complex heartbeat waveform. Further, the invention includes circuitry for comparing the frequency of the respiration signal with the frequency of the heartbeat signal, and thereby eliminating false indications of respiration which sometimes occur through misinterpretation of the heartbeat signal as a respiration signal. Further, the invention includes alarm circuits for generating audible and other alarms upon detection of the apneic condition, and limit and rate control circuits for providing system sensitivity over predetermined heartbeat and respiration frequencies.

It is a principal object of the present invention to provide a system for monitoring heartbeat and respiration, and for processing signals representative thereof to provide an alarm when an apneic condition exists while preventing false alarms caused by false processing of received signals.

It is another object of the present invention to detect apparent heartbeat and respiration signals occurring at the same frequency, and to generate an apnea alarm when such conditions exist.

It is a further object to provide an apnea monitoring system having provision for setting an upper and lower bound for the rate of reception of heartbeats.

It is yet another object of the present invention to provide signals for monitoring the presence of either respiration or heartbeat.

It is a further object of the present invention to provide an apnea monitoring system having automatic circuit fault detection for identifying malfunctions within the system itself.

BRIEF DESCRIPTION OF THE DRAWINGS

The foregoing and other objects will become apparent from the appended specification and claims, and with reference to the drawings, in which:

DETAILED DESCRIPTION OF THE INVENTION

Figure 1:
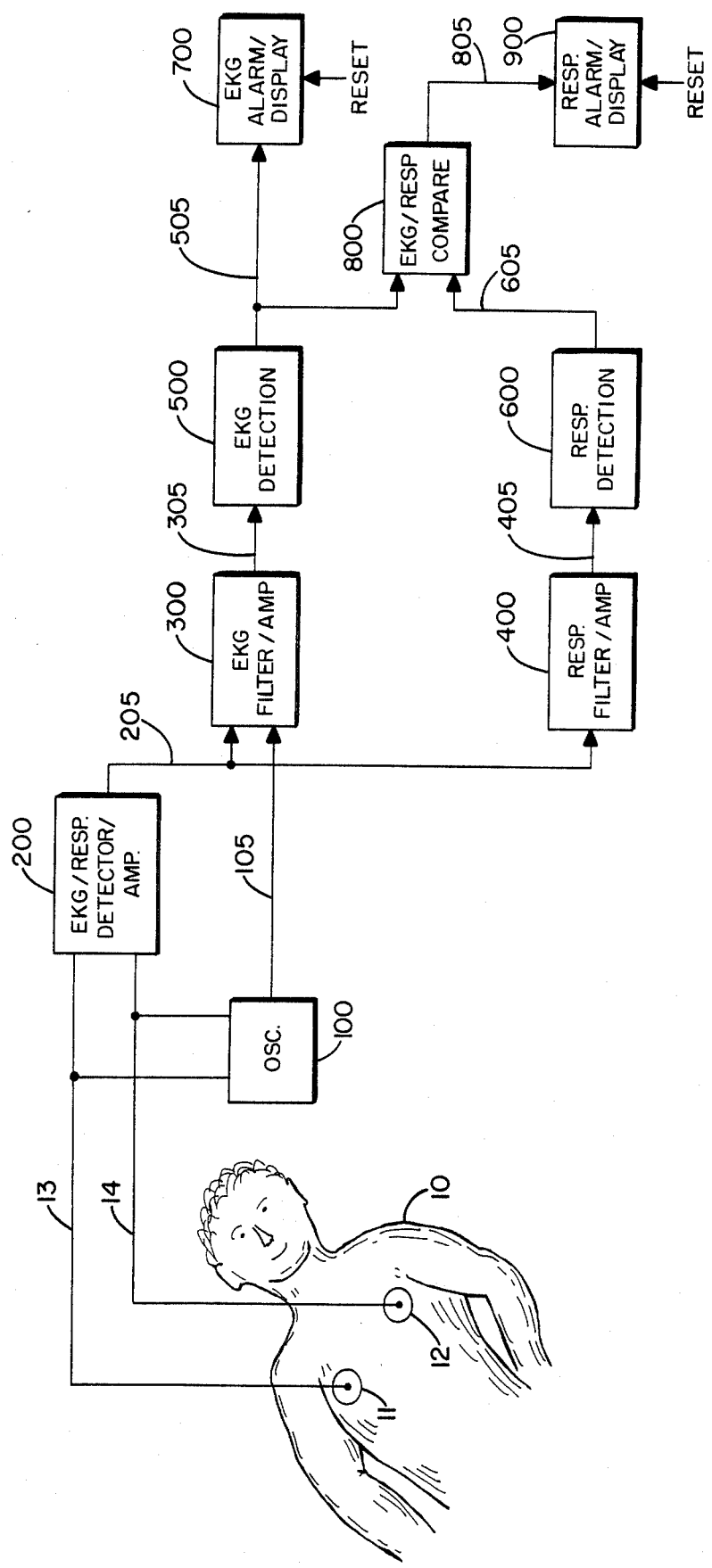
FIG. 1 shows a simplified diagram of the apparatus.

Referring first to FIG. 1, there is shown a simplified diagram of the apparatus attached to a patient 10. A pair of electrodes 11 and 12 are connected through suitable wires 13 and 14 to an oscillator 100 and a detector/amplifier circuit 200. Oscillator 100 develops a relatively low frequency carrier signal, on the order of 30 kilohertz (kHz), which signal is presented to wires 13 and 14, and is received by detector/amplifier circuit 200. Electrodes 11 and 12 receive minute electrical signals generated within the patient 10, which signals are electrocardiac signals representative of heartbeat. Further, the impedance through patient 10 varies with patient respiration, and these impedance changes are detected by electrodes 11 and 12, in combination with the carrier frequency currents transmitted to patient 10 by oscillator 100, and result in a slowly varying amplitude change to the carrier frequency as respiration progresses. Thus, the signals received by detector/amplifier circuit 200 contain a signal in correspondence with electrocardiac information (EKG), and also an amplitude modulated 30 kHz frequency corresponding to respiration. All of these signals are amplified within detector/amplifier circuit 200.

The output of detector/amplifier circuit 200 is fed into an EKG filter/amplifier 300 and into a respiration filter/amplifier 400. The EKG filter/amplifier 300 filters out unwanted signals and develops an EKG signal which is fed into an EKG detection circuit 500. The respiration filter/amplifier 400 similarly filters out unwanted signals and feeds a signal representative of respiration into respiration detection circuit 600.

The output of EKG detection circuit 500 is fed into an alarm/display circuit 700, wherein indications of EKG presence are developed, and an alarm signal is sounded in the absence of EKG signals. Further, the output of EKG detection circuit 500 is fed into a comparator circuit 800, where its signals are compared against the signals of the respiration detection circuit 600 output. Respiration detection circuit 600 also is connected to a respiration alarm/display circuit 900, which provides visible indication of the presence of respiration and an alarm when respiration ceases. The EKG/respiration comparator circuit 800 suppresses the respiration signal whenever the frequencies of the EKG signal and the respiration signal are identical, within a prescribed range, and this lack of output signal is coupled to respiration alarm/display circuit 900.

Figure 2:
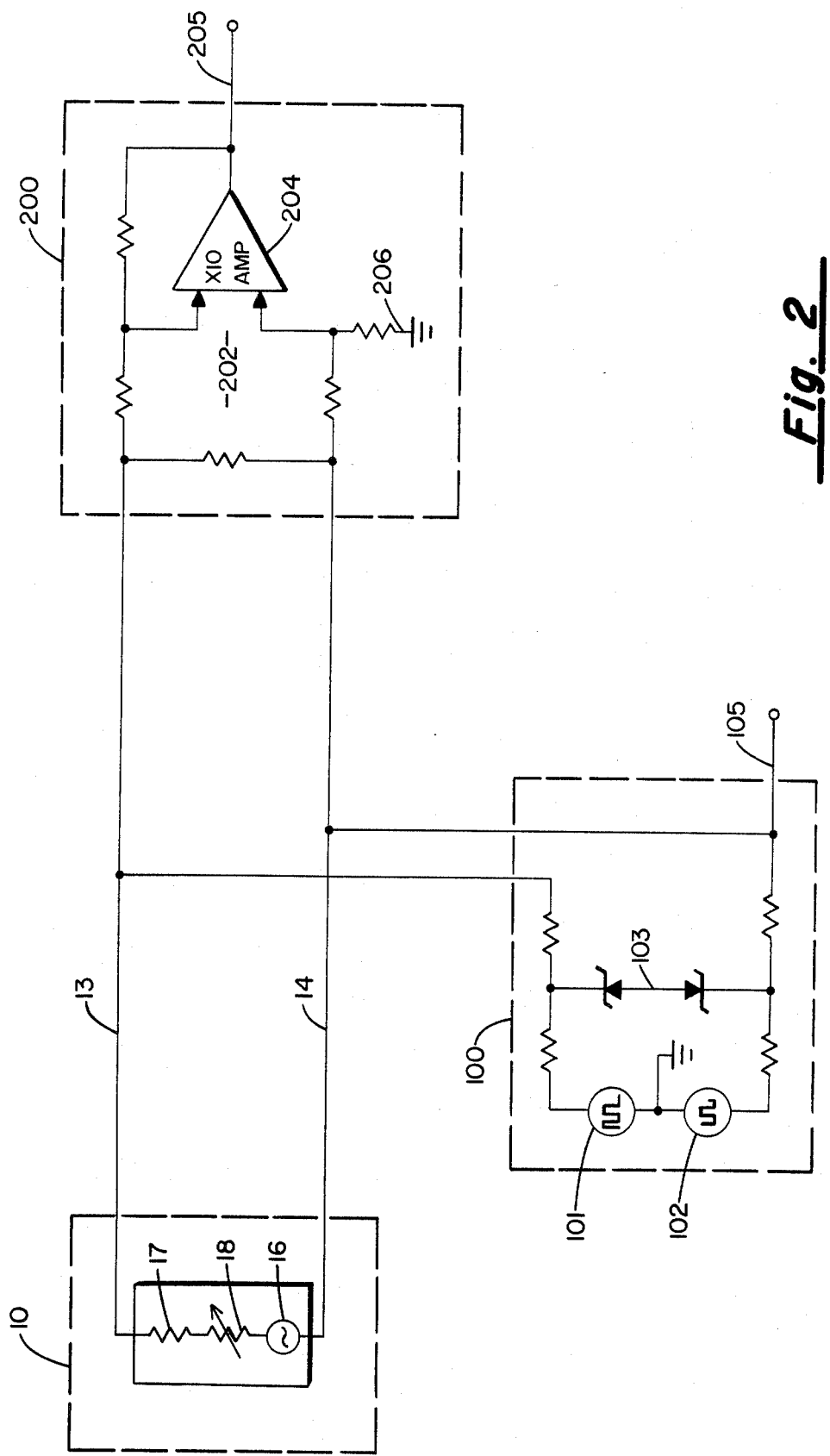
FIG. 2 shows a schematic diagram of certain of the circuits represented in FIG. 1.

FIG. 2 shows a schematic diagram of certain of the circuits represented in FIG. 1. For purposes of explanation, patient 10 is represented as an equivalent electrical circuit comprising an internal voltage generator 16, an internal fixed impedance 17, and an internal variable impedance 18. The signal developed by voltage generator 16 and fixed impedance 17 is representative of heartbeat activity, and the variable impedance 18 represents impedance changes which occur during respiration of patient 10.

Oscillator 100 is shown in simplified schematic form, having two inverted-phase voltage generators 101 and 102 operating at a predetermined frequency. Voltage generators 101 and 102 develop respective signals through resistor networks, which signals are voltage-limited by voltage limiter 103 and coupled to wires 13 and 14.

Detector/amplifier circuit 200 receives the modulated signals coupled over wires 13 and 14, and transmits the received signals through a resistor network 202 to the input of an amplifier 204. Amplifier 204 has been selected to provide an amplification of approximately an order of magnitude, such that the output signal on line 205 is approximately 10 times the amplitude of the received input signals, and is referenced with respect to a common or ground point 206.

Figure 3:
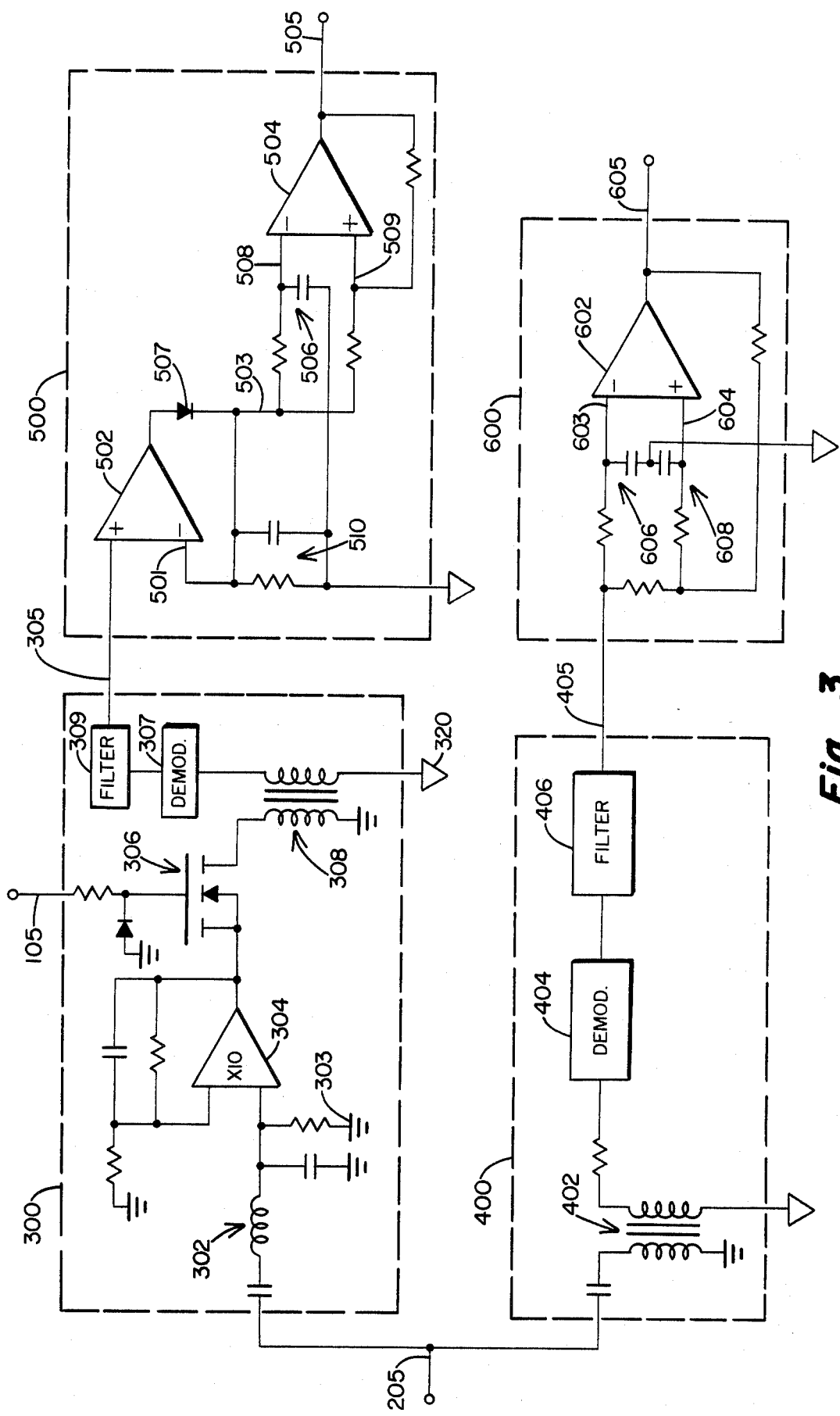
FIG. 3 shows a schematic diagram of certain additional circuits represented in FIG. 1.

FIG. 3 shows simplified schematic diagrams of certain additional circuits represented in FIG. 1, particularly EKG filter/amplifier circuit 300, respiration filter/amplifier circuit 400, EKG detection circuit 500, and respiration detection circuit 600. Grounded or common signal paths are shown schematically in two different formats in the drawings. The symbol of which 303 is an example shows common connections within a particular circuit, and the symbol 320, and other similar symbols, denote connections common to all circuits. Circuit 300 generally includes a filter network 302 and amplifier 304, which filters out the carrier frequency components received on line 205. The resultant EKG signal is fed into amplifier 304, where it is amplified by approximately an order of magnitude. The output of amplifier 304 is fed into a chopper circuit 306, which chopper circuit has a 30 kHz input signal via line 105 from oscillator 100, thereby causing it to operate at the carrier frequency. The output of chopper 306 is an EKG waveform chopped into 30 kHz pulses by the circuit 306. These signals are fed into a transformer 308, where they emerge as a series of amplitude-variant pulses which are fed into a demodulator 307 and filter/amplifier 309, and then to output line 305.

The pulses on line 305 are fed into EKG detection circuit 500, specifically into amplifier 502. The diode 507 and resistor-capacitor feedback circuit 510 of amplifier 502 causes a single output pulse to appear on line 503 for each EKG pulse signal received by circuit 500. Diode 507 rectifies the output signal from amplifier 502, and resistor-capacitor circuit 510 integrates this rectified signal to provide the line 503 signal. The signal on line 503 is coupled into the positive input of amplifier 504 via line 509, which amplifier 504 is connected as a comparator amplifier and trigger circuit. The signal received at the negative input of amplifier 504 via amplifier input line 508 is integrated by R-C circuit 506 and thus is slightly time-delayed by virtue of the R-C input circuit 506, and is also voltage-attenuated relative to the signal on line 503. This signal is compared against the signal received on line 509, and amplifier 504 generates an output whenever the signal on line 509 exceeds the signal on input 508. This results in an output signal on line 505 which is a single pulse for each EKG signal received by the system.

The input to respiration filter/amplifier circuit 400 is received via line 205. The input signal is transformer-coupled via transformer 402 to a demodulator 404. Demodulator 404 retrieves the slowly-varying respiration signal from the EKG signal present in the raw signal waveform, and feeds the respiration signal riding on the carrier frequency into filter 406. Filter 406 removes the carrier frequency components from the received signal, amplifies the resultant respiration waveform, and transmits a signal representative of respiration to output line 405.

The output signal from line 405 is fed to respiration detection circuit 600, and is used to drive two inputs to a comparator amplifier 602. Input line 603 receives a first respiration signal, through R-C network 606, and input line 604 receives a second, delayed and voltage offset respiration signal through R-C network 608. Input line 603 is connected to the negative input terminal of comparator amplifier 602, and input line 604 is connected to the positive input terminal of comparator amplifier 602. Amplifier 602 generates an output signal whenever the signal on line 604 exceeds the signal on line 603. This output signal is transmitted to output line 605, and is representative of the occurrence of a respiration event.

Figure 4:
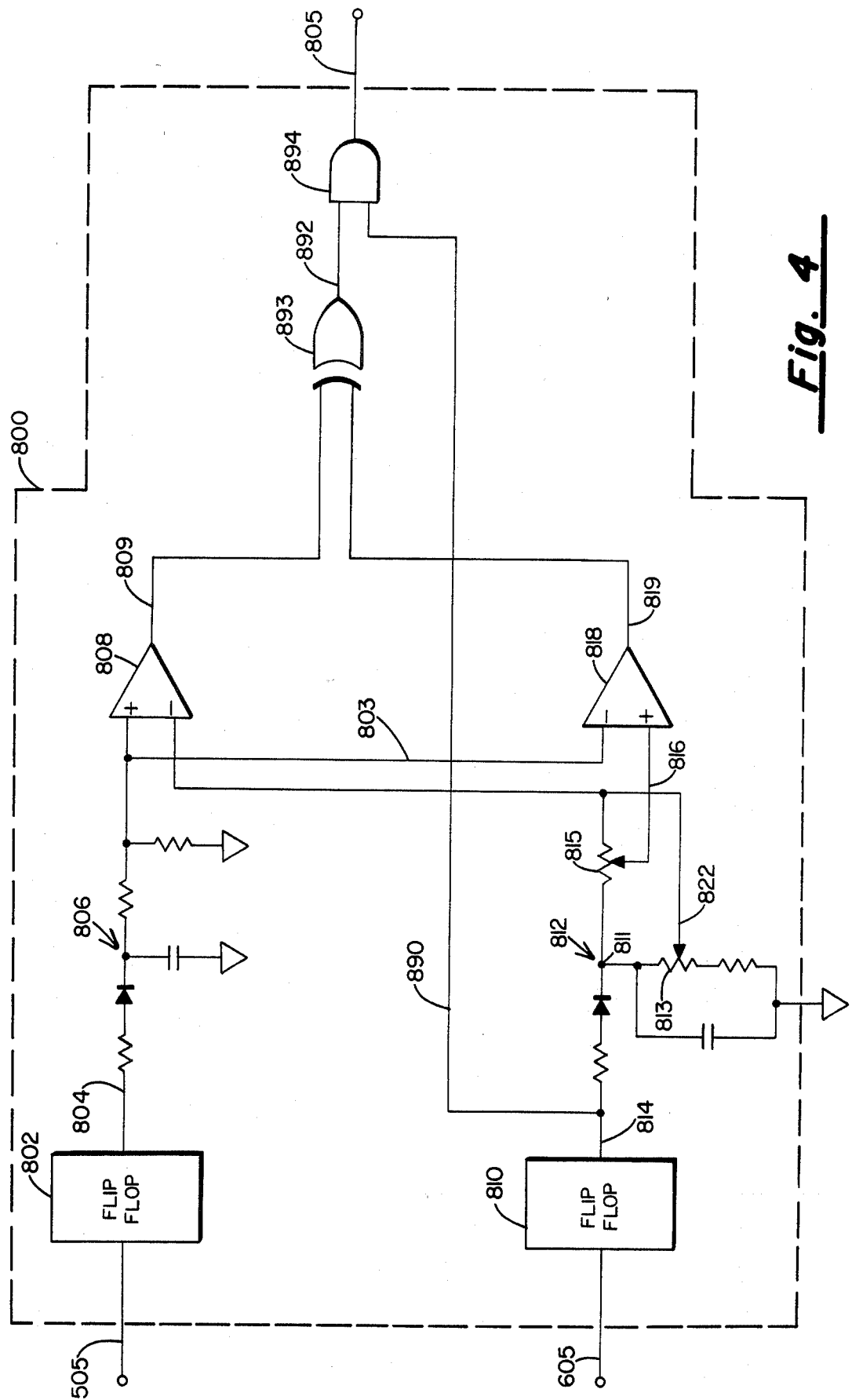
FIG. 4 shows a schematic diagram of certain additional circuits represented in FIG. 1.

Referring next to FIG. 4, the EKG/respiration comparator circuit 800 is shown. This circuit receives inputs from each of the detection circuits 500 and 600, via lines 505 and 605 respectively, and generates an output signal at line 805 which is representative of a detected apnea condition. Input line 505 is received by a monostable flip-flop circuit 802. Circuit 802 developes a single output pulse at line 804 for each EKG input signal received on line 505. The amplitude and time duration of this pulse are constant, regardless of the variations in the received input signal. The signal on line 804 is transmitted via an input network 806 to a comparator/amplifier circuit 808. Network 806 provides an average DC voltage signal input to comparator/amplifier 808, the magnitude of which is directly proportional to heartbeat rate.

The signal on line 605 is transmitted to a monostable flip-flop circuit 810. Circuit 810 develops a single pulse of fixed amplitude and duration at output line 814, for each respiration signal received via input line 605. The signal on line 814 is transmitted through network 812 to both comparators/amplifiers 808 and 818. Network 812 converts the pulse signal on line 814 to an average DC voltage signal, the magnitude of which is representative of the respiration rate. This voltage is present at junction 811, and it appears across a resistor network including variable resistor 813. A portion of this voltage is tapped off at line 822 and is coupled to circuit 808 as a second comparator input. The average DC voltage signal at junction 811 is also developed across the resistor network including variable resistor 815, and a portion of this signal is developed at line 816 and is fed into comparator 818 as a second input comparison voltage. The voltage level at line 816 is always higher than the voltage level at line 822, by an amount predetermined by the setting of variable resistor 815. Thus, the respiration voltage fed to comparator 808 via line 822 is representative of a respiration rate, and the voltage input fed into comparator 818 via line 816 is representative of a predetermined higher respiration rate. The respective respiration voltage levels are compared in comparators 808 and 818 with voltages representative of the heartbeat rate, to develop signals as will be hereinafter described.

Comparator 808 generates an output signal when the actual sensed heartbeat rate exceeds the respiration signal on line 822. Comparator 818 generates an output signal on line 819 whenever the respiration rate voltage on line 816 exceeds the heartbeat voltage rate on line 803. The only time that a signal will appear on both lines 809 and 819 is when the signal representative of heartbeat rate lies within the narrow range of values of the signals representative of the two respiration rates developed on lines 816 and 822. The two respiration rate signals on lines 816 and 822 are artificially developed upper and lower respiration rate signals.

The signals on lines 809 and 819 are coupled into an "Exclusive Or" logic circuit 893. The output from the circuit 893 is developed when either input line contains a signal, but not when *both* input lines contain a signal, and also not when *both* input lines contain no signals. When the respiration rate range, as artificially developed and described above, is lower or greater than the heart rate, line 892 receives a signal, which signal is combined with the signal from line 890 into an "And" gate 894. When signals are present on both lines 890 and 892, gate 894 permits an output signal to appear on line 805. The signal on line 890 is representative of the receipt of a respiration signal, and is therefore in time coincidence with the receipt of each respiration signal. Thus, circuit 800 functions to receive as inputs respective signals representative of a heartbeat event and representative of a respiration event. Circuit 800 generates an output signal whenever a respiration event occurs, providing that at the time of such occurrence the rate of respiration and the rate of heartbeat are not synchronous, within predetermined parameters. The signal on line 805 is therefore representative of a "safe condition", and the absence of a signal on line 805 is representative of an apnea condition.

Figure 5:
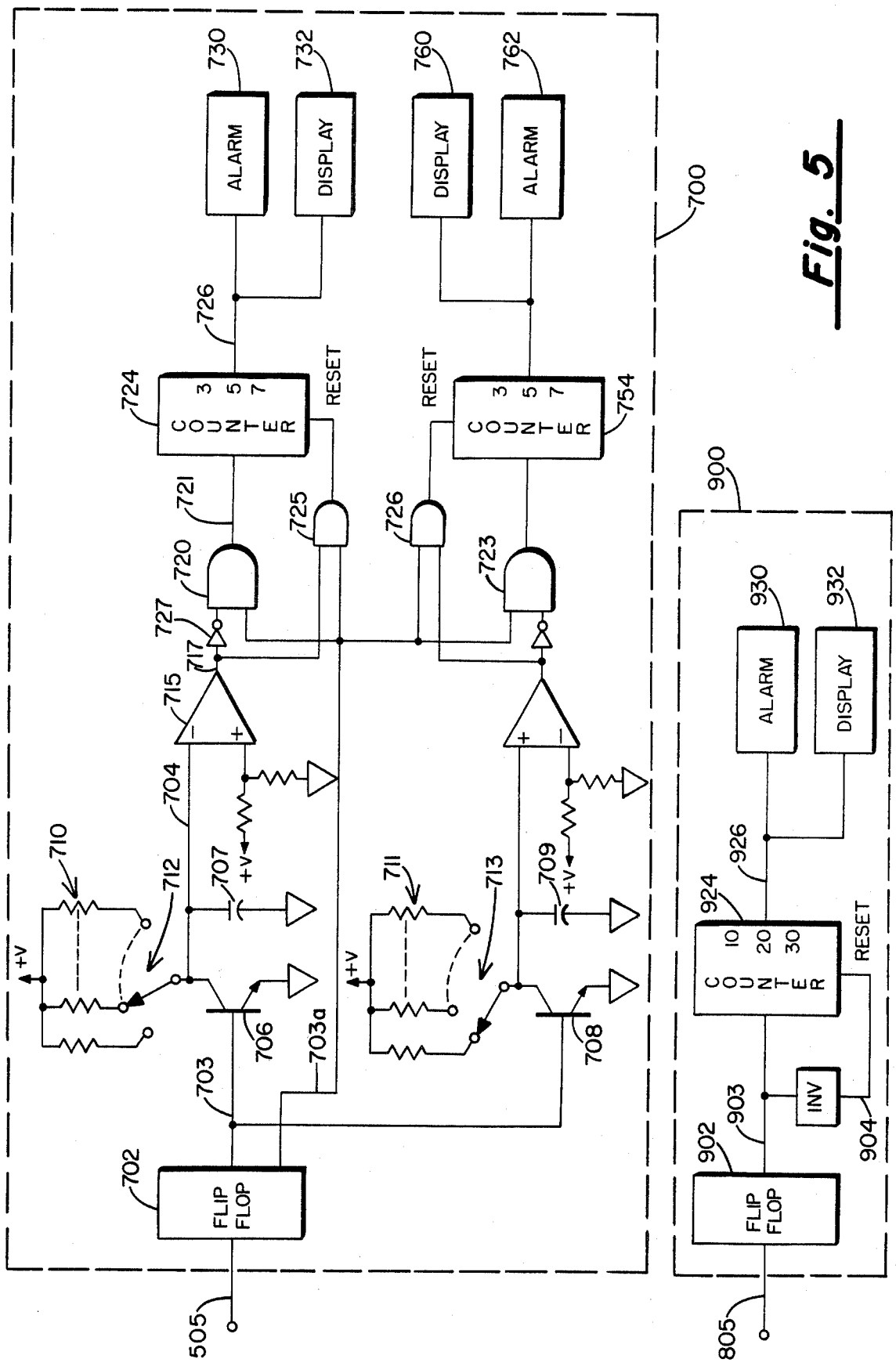
FIG. 5 shows a schematic diagram of certain additional circuits represented in FIG. 1.

Referring next to FIG. 5, there is shown alarm/display circuits 700 and 900. Alarm/display circuit 700 receives a signal via line 505 to a dual monostable flip-flop circuit 702. The signal received via line 505 is representative of a heartbeat (EKG) signal. The output signal from monostable circuit 702 first appears on line 703a, and is a signal of predetermined amplitude and duration, approximately five microseconds, which is simultaneously applied to "And" gates 720, 723, 725 and 726. The signal on line 703a is sequentially followed by a 165 microsecond signal, which is applied to simultaneously turn on transistors 706 and 708 for the time duration which the pulse remains on line 703. Transistor 706 discharges capacitor 707, and transistor 708 discharges capacitor 709. Capacitor 707 receives a voltage charge by virtue of current flow through one of the resistors in resistor network 710, as selected by switch 712. Capacitor 709 receives a voltage charge by virtue of current flow through one of the resistors in resistor network 711, as selected by switch 713. The respective resistors in resistor network 710 are approximately three times the magnitude of corresponding resistors in resistor network 711. Resistor network 710 is identified as a "preset low" heart rate selector, and resistor network 711 is identified as a "preset high" heartbeat selector.

Since the circuits associated with transistors 706 and 708 function essentially similarly, the description of one of them will suffice. Switch 712 is a selector switch adapted for electrically connecting in series arrangement one of the resistors in resistor network 710 with capacitor 707. One switch 712 has been set to a preselected position, capacitor 707 begins voltage charging at a rate determined by the RC time constant of the selected resistor and capacitor 707. However, each time an EKG signal is received via input line 505, line 703 generates a 165 microsecond "on" signal to transistor 706. This short duration "on" signal causes transistor 706 to effectively short circuit the voltage charge in capacitor 707, thereby discharging it. Immediately after each EKG signal has been received transistor 706 again turns off and the resistance/capacitance charging effect again begins. The voltage on line 704 is therefore a DC voltage whose magnitude is a function of the length of time since the last EKG signal has been received. This voltage is fed into comparator 715, and is compared against a fixed DC reference potential at the other comparator input. Whenever the voltage on input line 704 exceeds the reference voltage, coparator 715 generates an output signal on line 717. This signal is inverted by inverter 727 and is connected to an "And" gate 720, the other input being the signal on line 703a. The coincidence of a signal on line 703a and a signal on line 717 results in a signal on line 721 which causes counter 724 to increment one count. Counter 724 may be manually preset so as to provide an output signal on line 726 at any time its accumulated count has reached any of several predetermined quantities. For example, counter 724 may be set to generate an output signal at a count of "3", "5", or "7". When a signal is generated on line 726, it activates an audible alarm 730 and a visual display 732. Alarm 730 and display 732 are associated with the indication of Bradycardia, or slow heartbeat.

The circuits associated with transistor 708, through and including display 760 and alarm 762, function in essentially the same manner as has been hereinbefore described. The essential difference between the circuits associated with transistor 706 and those associated with 708 is in that the resistances in resistor network 711 are respectively essentially one-third the value of each of the resistances in resistor network 710. This results in the charging of capacitor 709 at a faster rate than the charging of capacitor 707. Therefore, the circuits associated with transistor 708 are associated wtih a rapid heartbeat alarm, otherwise known as Tachycardia.

The function of counter 724 and 754 is to accumulate counts of successive EKG events which are respectively lower than a preset value or higher than a preset value. Each of these counters will accumulate only the successive number of such low or high heartbeat occurrences, and if an intermediate heartbeat occurs which lies within the acceptable range both counters will become automatically reset. Thus, the counters do not activate their respective alarms until a number of successive slow or fast heartbeats have occurred, but which are not interspersed with more or less normal heartbeats.

FIG. 5 also shows alarm and display circuit 900, which receives an input from line 805 whenever a respiration event has occurred. Monostable flip-flop 902 generates an output signal on line 903 whenever a signal is received on input line 805. The signal on 903 is coupled into a free running oscillator/counter 924, which measures the length of time since the last respiration event occurred. As soon as an apnea event is detected, by absence of a signal on line 903, counter 924 begins accumulating count in real time, and when a predetermined real time count value has beem accumulated counter 924 generates a signal on line 926. The actual predetermined count time may be manually selected over a varying range of time. For example, counter 924 may be set to accumulate count for 10 seconds–30 seconds, or increments therebetween. In the event the apnea event disappears during the course of count accumulation, the signal on line 903 occurs, and an inverted signal on line 904 resets counter 924. As soon as the accumulated count has resulted in the generation of a signal on line 926, an audible alarm 930 is activated and a visual display 932 is also activated.

Figure 6A:
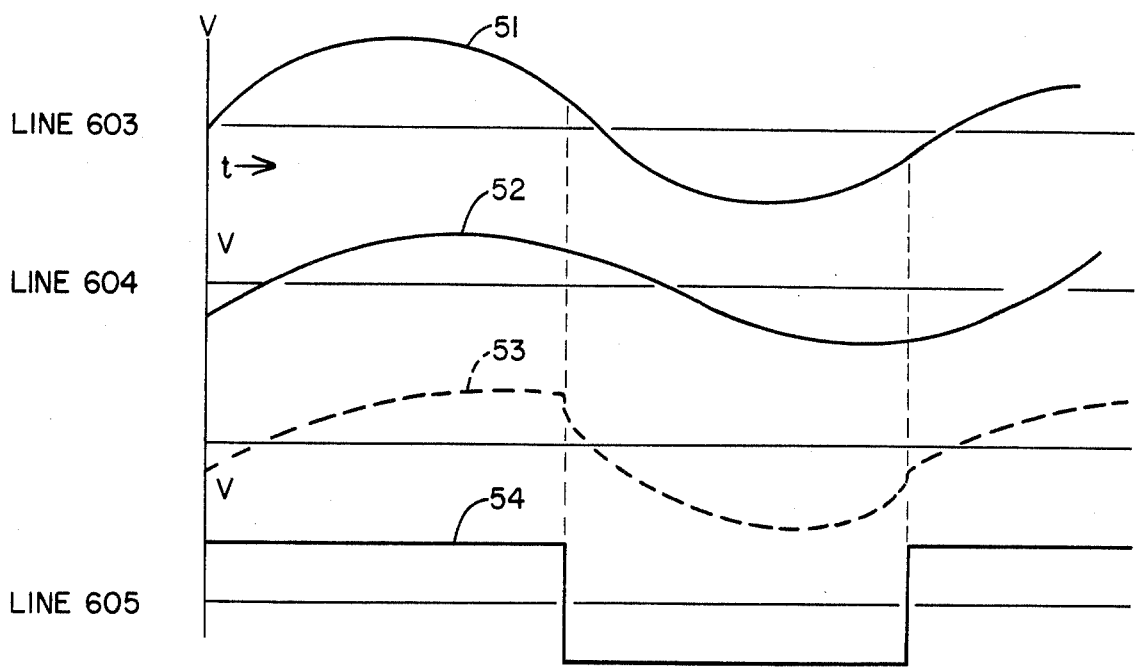
FIGS. 6A and 6B show electrical waveforms pertinent to the present invention.

Referring to FIG. 6A, certain waveforms are shown which are relevant to the operation of the respiration detection circuit 600. Curve 51 shows a typical respiration waveform, usually having a time period in the range of two–twenty seconds. Specifically, curve 51 shows a respiration voltage at line 603 (see FIG. 3), which is an input to comparator amplifier 602. Curve 52 shows a time-shifted respiration waveform, including some voltage offset, which is present at line 604, the other input to amplifier 602. Curve 53 shows the effects of the resistive feedback network of amplifier 602 on the signal waveform at input line 604. Curve 53 is illustrative of the "hysteresis" effect which is caused by the circuits connected to amplifier 602, giving rise to certain triggering offset voltages whenever the curves 51 and 52 reach a cross-over point. Curve 54 illustrates the signal on line 605, which is the output of the respiration detection circuit 600.

Figure 6B:
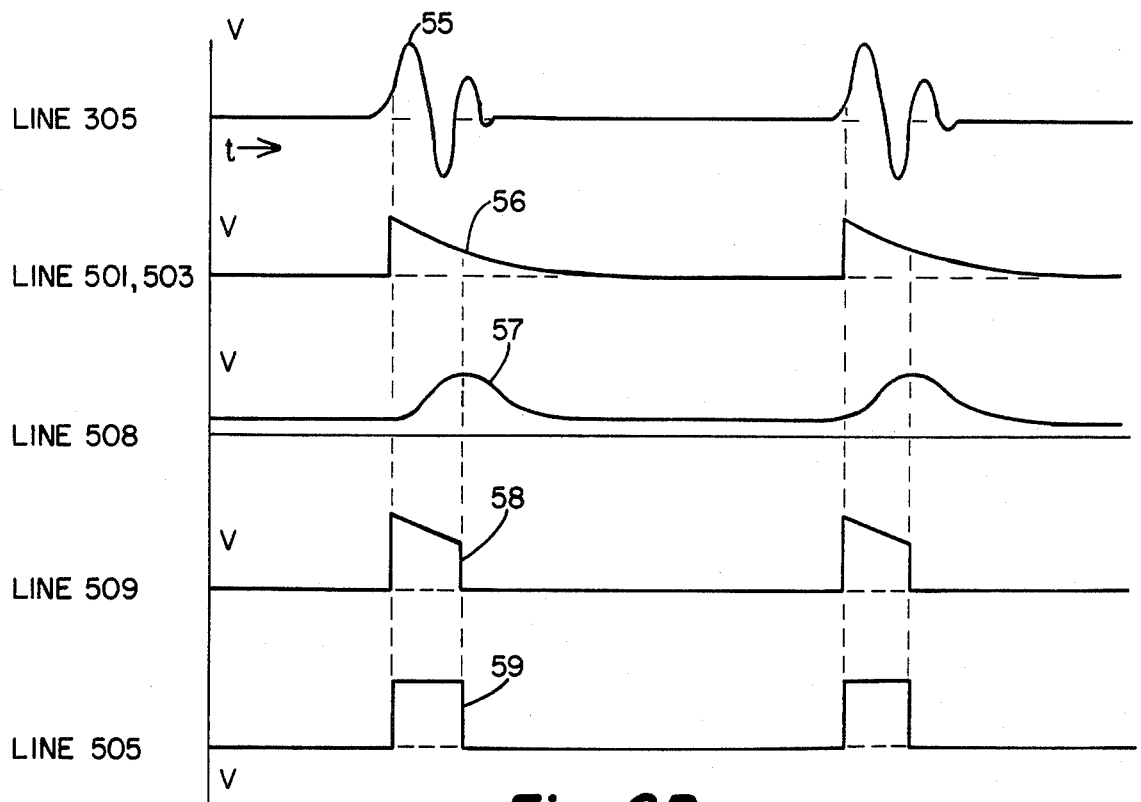

FIG. 6B shows pertinent waveforms which may be found within the EKG detection circuit 500. For example, cirve 55 is a representation of an EKG voltage waveform at line 305 (see FIG. 3). Curve 56 is representative of the voltage at lines 501 and 503, caused by the resistor-capacitor-diode feedback from amplifier 502. It should be noted on FIG. 6B that the rectified and integrated waveform represented by curve 56 extends longer than the time interval of the EKG waveform represented by curve 55. This provides the blanking signal described hereinbefore, to eliminate spurious signals generated by the complex EKG waveform. Curve 57 represents an integrated and reduced amplitude waveform derived from curve 56 by operation of R-C network 506, and applied at the input line 508 of amplifier 504. Curve 58 represents the voltage at line 509, which is the portion of curve 56 which exceeds the voltage of curve 57. Finally, curve 59 illustrates the output voltage pulse on line 505, which is representative of an EKG event.

In operation, the invention is coupled to a patient using conventional electrodes or other similar coupling mechanisms which enable measurement of conductivity and electrical characteristics of the human body. The invention continuously receives signals from the body which are broken down and analyzed as has been described herein, to provide a visual indication of each heartbeat and each respiration event. An upper and lower preset may be adjusted to monitor heartbeat, thereby generating an audible and/or visual alarm whenever the monitored heartbeat falls outside the preset range. Respiration events are monitored, and the time between respiration events is compared against a preselected time standard, such that when the time between two respiration events exceeds the preselected time an apnea condition is recorded and an audible and/or visual alarm is sounded.

The invention contains special circuits to make comparison of the rate of received heartbeats against the rate of received respiration events. These special circuits protect against misinformation which otherwise could occur, such as a condition where patient breathing has altogether ceased but heartbeat continues for a limited time. To guard against the possibility that the invention may receive and record the heartbeat as both a heartbeat signal and a respiration signal, the special circuits make a comparison of the rates of these two received signals. If the rates of the two signals are different by more than a predetermined rate range the circuits determine that the signals are indeed derived from two separate input signals. However, if the rates of the two signals are within a predetermined range of similarity the circuits determine that they are derived from a single external signal, and an apnea alarm is sounded.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. An apparatus for monitoring patient respiration and heartbeat, comprising
   (a) sensor means adapted for coupling to said patient for sensing composite electrical signals representative of said patient heartbeat and respiration;
   (b) oscillator means for generating a carrier frequency, coupled to said sensor means;
   (c) detector means for receiving and detecting said heartbeat and respiration signals, coupled to said sensor means and said oscillator means;
   (d) heartbeat detection circuit, coupled to said detector means, said heartbeat detection circuit having means for developing a first single signal responsive to each detected heartbeat; including a first circuit for generating a detected heartbeat signal and for rectifying said signal, a second circuit for receiving said rectified signal and generating a time-decaying signal therefrom, said time-decaying signal having a greater time duration than said detected heartbeat signal, and a circuit means for receiving said time-decaying signal and generating an intergrated pulse signal therefrom, and a comparator circuit means for receiving said time-decaying signal and said integrated pulse signal and generating said first single signal when said time-decaying signal is greater than said integrated pulse signal;
   (e) respiration detection circuit, coupled to said detector means, said respiration detection circuit having means for developing a second single signal responsive to each detected respiration; including a first integrator circuit for developing a first integrated respiration signal and a second integrator circuit for developing a second integrated respiration signal time delayed relative to said first integrated respiration signal, and a circuit for receiving said first and second integrated respiration signals and for developing said second single signal when said first integrated respiration signal is greater than said second integrated respiration signal; and
   (f) heartbeat alarm circuit coupled to receive said first single signal responsive to each detected heartbeat, said heartbeat alarm circuit having means for presetting a minimum and maximum heartbeat rate and having means for developing a received heartbeat rate signal responsive to said first single signals, and having means for generating an alarm when said received heartbeat rate signal falls below said minimum or above said maximum preset heartbeat rate.

2. An apparatus for monitoring patient respiration and heartbeat and for generating alarm signals under predetermined conditions of heartbeat and respiration, comprising
   (a) sensor means adapted for coupling to said patient for sensing composite electrical signals representative of said patient heartbeat and respiration;
   (b) oscillator means for generating a carrier frequency, coupled to said sensor means;
   (c) detector means for receiving and detecting said heartbeat and respiration signals, coupled to said sensor means and said oscillator means;
   (d) heartbeat detection circuit, coupled to said detector means, said heartbeat detection circuit having means for developing a first single signal responsive to each detected heartbeat; including means for developing a signal representative of said heartbeat, means for rectifying said representative signal, means for time decaying said rectified representative signal over a time duration longer than said signal representative of said heartbeat and for developing a blanking signal, means for integrating said blanking signal to develop an integrated pulse signal, means for receiving and comparing said blanking signal and said integrated pulse signal and for developing said first single signal during the time when said blanking signal is greater than said integrated pulse signal;
   (e) respiration detection circuit, coupled to said detector means, said respiration detection circuit having means for developing a second single signal responsive to each detected respiration; including means for developing a signal representative of said detected respiration, first means for integrating said representative signal to develop a first integrated signal, second means for integrating said representative signal to develop a second integrated signal, said second integrated signal being time delayed relative to said first integrated signal, means for comparing said first integrated signal and said second integrated signal and for developing said second single signal when said first integrated signal is greater than said second integrated signal;
   (f) heartbeat alarm circuit coupled to receive said single signal responsive to each detected heartbeat, said heartbeat alarm circuit having means for presetting a minimum and maximum heartbeat rate and having means for developing a first heartbeat rate signal responsive to said first single signals, and having means for generating an alarm when said first heartbeat rate signal falls outside either of said minimum or said maximum preset heartbeat rate; and (g) respiration alarm circuit coupled to receive said single second signal, said respiration alarm circuit having means for developing a respiration rate signal responsive to said second single signals, and having means for comparing said respiration rate signal with said heartbeat rate signal, and having means for generating an apnea alarm when said heartbeat rate signal and said respiration rate signal are substantially equal.

3. The apparatus of claim 2, further comprising timer means coupled to said respiration alarm circuit, for generating a further alarm signal a predetermined time after said apnea alarm has been generated.

4. An apparatus for monitoring signals representative of patient respiration and heartbeat and for processing said signals to generate alarm signals under predetermined conditions of respiration and heartbeat, comprising (a) sensor means adapted for coupling to said patient for generating composite electrical signals representative of said patient heartbeat and respiration;

(b) first detector means coupled to said sensor for receiving said sensor composite signals and for detecting and separating therefrom signals representative of heartbeat, and for generating a single first signal for each detected heartbeat signal comprising means for rectifying said detected heartbeat signal and for generating a time-decaying signal from said rectified heartbeat signal, said time-decaying signal extending for a longer time duration than said heartbeat signal; said means for generating a single first signal further comprising means for integrating said time-decaying signal and means for comparing said time-decaying signal and said integrated time-decaying signal and for generating said single first signal during the time period when said time-decaying signal is greater than said integrated time-decaying signal;

(c) second detector means coupled to said sensor for receiving said sensor composite signals and for detecting and separating therefrom signals representative of patient respiration, and for generating a single second signal for each detected respiration signal, comprising first integrating means for generating a first integrated respiration signal and second integrating means for generating a second integrated respiration signal, said second integrated respiration signal being time delayed relative to said first integrated respiration signal; said means for generating a single second signal further comprising means for comparing said first and second integrated respiration signals and for generating said single second signal during the time period when said first integrated respiration signal is greater than said second integrated respiration signal;

(d) first rate detection circuit means coupled to receive said first signal, for generating a first rate signal representative of the time rate of receiving said first signal;

(e) second rate detection circuit means coupled to receive said second rate signal, for generating a second rate signal representative of the time rate of receiving said second signal; and (f) comparison means coupled to receive said first rate signal and said second rate signal and for generating an apnea signal when said first and second rate signals are equal within predetermined limits;

(g) EKG alarm circuit means coupled to receive said first detector means first signal, for generating an EKG alarm when the repetition rate of said first signal is outside of a preselected range of repetition rates; and (h) respiration alarm circuit means coupled to receive said apnea signal from said comparison means, for generating an apnea alarm signal when said apnea signal is present for greater than a predetermined time duration.

5. The apparatus of claim 4, wherein said sensor means further comprises an oscillator means for generating a fixed frequency signal as a carrier for said electrical signals representative of patient respiration.

6. The apparatus of claim 4, wherein said EKG alarm circuit means further comprises a first comparison means for comparing the repetition rate of said first signal with a first predetermined signal representative of a low repetition rate, and for generating an EKG alarm when said first signal repetition rate falls below said low repetition rate.

7. The apparatus of claim 6, wherein said EKG alarm circuit further comprises a second comparison means for comparing said first signal repetition rate with a second predetermined signal representative of a high repetition rate, and for generating an EKG alarm when said first signal repetition rate exceeds said high repetition rate.

8. The apparatus of claim 5, wherein said first detector means further comprises means for filtering said oscillator signal from said composite signals.

9. The apparatus of claim 8, wherein said second detector means further comprises means for filtering said oscillator signal from said composite signals.

10. The apparatus of claim 9, further comprising EKG alarm circuit means coupled to receive said first detector means first signal, for generating an EKG alarm when said first signal repetition rate falls outside a preselected range of repetition rates.

11. The apparatus of claim 10, further comprising respiration alarm circuit means coupled to receive said apnea signal from said comparison means, for generating an apnea alarm signal when said apnea signal exceeds a predetermined time duration.

12. The apparatus of claim 11, wherein said EKG alarm circuit means further comprises a first comparison means for comparing the repetition rate of said first signal with a first predetermined signal representative of a low repetition rate, and for generating an EKG alarm when said first signal repetition rate falls below said low repetition rate.

13. The apparatus of claim 12, wherein said EKG alarm circuit further comprises a second comparison means for comparing the repetition rate of said first signal with a second predetermined signal representative of a high repetition rate, and for generating an EKG alarm when said first signal repetition rate exceeds said high repetition rate.

* * * * *